US012702762B2

(12) United States Patent
Melander et al.

(10) Patent No.: US 12,702,762 B2
(45) Date of Patent: Aug. 11, 2026

(54) ACTIVATION MECHANISM FOR DRUG DELIVERY DEVICE

(71) Applicant: AMGEN INC., Thousand Oaks, CA (US)

(72) Inventors: Matias Melander, Copenhagen (DK); Joshua Jay Dudman, Copenhagen (DK); Joseph Michael Iglesias, Santa Monica, CA (US); Bjarke Lykke Ludvig Svendsen, Slagelse (DK); Adam B. McCullough, Westlake Village, CA (US); Christian Plambech, Soeborg (DK); Steve Sanchez, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 725 days.

(21) Appl. No.: 17/261,648

(22) PCT Filed: Aug. 16, 2019

(86) PCT No.: PCT/US2019/046899
§ 371 (c)(1),
(2) Date: Jan. 20, 2021

(87) PCT Pub. No.: WO2020/037256
PCT Pub. Date: Feb. 20, 2020

(65) Prior Publication Data

US 2021/0260302 A1 Aug. 26, 2021

Related U.S. Application Data

(60) Provisional application No. 62/719,367, filed on Aug. 17, 2018.

(51) Int. Cl.
*A61M 5/315* (2006.01)
*A61M 5/20* (2006.01)
*A61M 5/32* (2006.01)

(52) U.S. Cl.
CPC ...... *A61M 5/31585* (2013.01); *A61M 5/2033* (2013.01); *A61M 5/3202* (2013.01); *A61M 2005/2013* (2013.01)

(58) Field of Classification Search
CPC ............ A61M 5/31585; A61M 5/2033; A61M 5/3202; A61M 2005/2013;
(Continued)

(56) References Cited

U.S. PATENT DOCUMENTS 5,451,210 A 9/1995 Kramer et al.
2005/0027255 A1 2/2005 Lavi et al.
(Continued)

FOREIGN PATENT DOCUMENTS

CN 106456907 A 2/2017
EP 2438941 A1 4/2012
(Continued)

OTHER PUBLICATIONS

International Search Report and Written Opinion of the International Searching Authority for International Application No. PCT/US2019/046899, dated Oct. 18, 2019.
(Continued)

*Primary Examiner* — Bhisma Mehta
*Assistant Examiner* — Fatimata Sahra Diop

(57) ABSTRACT

A drug delivery device includes a housing, an injection assembly at least partially disposed in the housing, a shield, and a drive assembly at least partially disposed in the housing and coupled with the injection assembly and the shield. The shield has an extended position where at least a proximal end thereof extends a distance beyond a proximal
(Continued)

end of the housing. The injection assembly includes a needle or cannula having an endpoint. Upon moving the shield axially towards the distal end of the housing a predetermined distance, a retraction profile commences whereby the drive assembly administers a medicament via the injection assembly. A peak resistance force is exerted within approximately the first 12 mm of axial movement of the shield.

25 Claims, 7 Drawing Sheets

(58) Field of Classification Search
CPC ........ A61M 2005/3267; A61M 5/3157; A61M 5/31571; A61M 5/31591
See application file for complete search history.

(56) References Cited

U.S. PATENT DOCUMENTS

| | | | | |
|---|---|---|---|---|
| 2007/0112310 | A1 | 5/2007 | Lavi et al. | |
| 2010/0137798 | A1* | 6/2010 | Streit | A61M 5/3257 604/110 |
| 2013/0237921 | A1* | 9/2013 | Lannan | A61M 5/50 604/198 |
| 2014/0046259 | A1* | 2/2014 | Reber | A61M 5/2033 604/136 |
| 2016/0228651 | A1* | 8/2016 | Plambech | A61M 5/31535 |
| 2017/0014575 | A1* | 1/2017 | Hansen | A61M 5/31585 |
| 2017/0143902 | A1* | 5/2017 | Hansen | A61M 5/3245 |
| 2018/0140783 | A1* | 5/2018 | Raday | A61M 5/3257 |
| 2018/0304024 | A1* | 10/2018 | Andersen | B21D 53/00 |
| 2020/0030536 | A1 | 1/2020 | Lannan et al. | |
| 2021/0308380 | A1* | 10/2021 | Travanty | A61M 5/326 |

FOREIGN PATENT DOCUMENTS

| | | | |
|---|---|---|---|
| EP | 2606925 | A1 | 6/2013 |
| JP | 2017519581 | A | 7/2017 |
| WO | WO-2008/113864 | A1 | 9/2008 |
| WO | 2020/036717 | A2 | 2/2020 |

OTHER PUBLICATIONS

Second Office Action received in counterpart Chinese Patent Application No. 201980048699X, dated Feb. 1, 2023.
Third Office Action received in counterpart Chinese Patent Application No. 201980048699X, dated Jun. 14, 2023.
Fourth Office Action received in counterpart Chinese Patent Application No. 201980048699X, dated Oct. 11, 2023.
Office Action received in counterpart Israel Patent Application No. 279811, dated Sep. 27, 2023.
Office Action received in counterpart Japanese Patent Application No. 2020-573011, dated Jun. 20, 2023.
Chinese Patent Application No. 201980048699X, First Office Action, dated Jul. 8, 2022.
Examination Report received in counterpart Australian Patent Application No. 2019321678, dated Apr. 11, 2024.
Second Office Action received in counterpart Japanese Patent Application No. 2020-573011, dated Jan. 9, 2024.
Examination Report received in counterpart European Patent Application No. 19762544.5, dated Feb. 21, 2024.
Office Action received in counterpart Israel Patent Application No. 279811, dated Mar. 12, 2024.
Further Examiner's Report received in counterpart Australian Patent Application No. 2019321678, dated Jul. 8, 2024.
Third Office Action received in counterpart Japanese Patent Application No. 2020-573011, dated Jun. 18, 2024.
Office Action received in counterpart Mexican Patent Application No. MX/a/2021/001794, dated Jul. 31, 2024.
Second Office Action received in counterpart Mexican Patent Application No. MX/a/2021/001794, dated Mar. 19, 2025.

* cited by examiner

150
L
10
124a
110a
102a
110
102
122
184a
184
183
154
152
153
175
174
110b
170
160c
160
161
163
160d
190
180
182

160a
161a
160b
153a
155
163
152

ACTIVATION MECHANISM FOR DRUG DELIVERY DEVICE

CROSS-REFERENCE TO RELATED APPLICATION

Priority is claimed to U.S. Provisional Patent Application No. 62/719,367, filed Aug. 17, 2018, the entire contents of which are hereby incorporated by reference.

FIELD OF THE DISCLOSURE

The present disclosure generally relates to drug delivery devices and, more particularly, to mechanisms and methods of delivery and inserting or deploying a needle and/or cannula of a drug delivery device.

BACKGROUND

Drug delivery devices, such as injectors, are used to deliver liquid drugs to a patient. Upon activation, a drug delivery device will expel a drug stored within an internal reservoir through a needle, cannula, or other delivery member into the patient.

Some drug delivery devices, such as on-body injectors, may be temporarily attached to a patient to deliver a drug via an injection needle or some other means over an extended period of time. The drug delivery device may be adhesively attached to the tissue of the patient's abdomen, thigh, arm, or some other portion of the patient's body.

Some devices may have drawbacks. Specifically, users may be frightened by an exposed injection needle or feel they are inherently incapable of performing an injection. Because of aversions to exposed needles, as well as health and safety issues that may be involved, various types of injectors and other devices have been developed for concealing needles from the user and automating the injection task to assist the user in performing the injection, ensure reliable delivery of the medication and ensure patient safety.

Typically, three tasks may be performed when injecting a drug into a patient with a hypodermic syringe: 1) insertion of the needle into the patient; 2) injection of the drug from the syringe into the patient; and 3) withdrawal of the needle after the injection has been completed. For each task, the magnitude and direction of forces on the syringe, as well as the location of their application, may be different from the other tasks. For example, insertion of the needle may require the application of a minimal force on the syringe, for a very short period of time. On the other hand, injection of the medicament may require the application of a much greater force on the plunger of the syringe, and this force may need to be applied for a relatively longer period of time. Further, needle withdrawal may require the application of a force in an opposite direction from needle insertion. Accordingly, combining a desirable activation experience with a robust activation mechanism presents unique challenges. These, and other similar considerations, may become relevant when the injection process is to be automated.

Generally, shield-activated devices use manual needle insertion techniques whereby a user simultaneously inserts a needle and initiates dosing through the action of retracting a shield relative to the rest of the device. In these devices, the needle may automatically insert upon manually activating the device. Button-activated devices typically employ automated needle insertion mechanisms whereby the needle is inserted mechanically and the dosing mechanism release is automatically delayed until the correct device state is achieved. Any or all of these devices may use manual and/or automated withdrawal mechanisms to retract the needle. Each of these approaches may have relative benefits and shortcomings impacting user operation and satisfaction, and therefore, any combination of these approaches may also have associated benefits and shortcomings.

SUMMARY

In accordance with a first aspect, a drug delivery device includes a housing defining a shell, an injection assembly at least partially disposed in the housing, a shield, and a drive assembly at least partially disposed in the housing and coupled with the injection assembly and the shield. The shield has an extended position where at least a proximal end thereof extends a distance beyond a proximal end of the housing. The injection assembly includes a needle or cannula having an endpoint. Upon moving the shield axially towards the distal end of the housing a predetermined distance, a retraction profile commences whereby the drive assembly administers a medicament via the injection assembly. A peak resistance force is exerted within approximately the first 12 mm of axial movement of the shield. In some examples, the peak resistance force is exerted within approximately the first 8 mm of axial movement of the shield. Further, in some of these examples, the peak resistance force is exerted within approximately the first 3 mm of axial movement of the shield.

In some examples, the drive assembly includes a container disposed within the shell, a nut disposed within the shell and positioned adjacent to the second end of the container, a trigger ring disposed within the shell, a plunger rod guide disposed within the shell, and a plunger rod at least partially disposed within the opening of the plunger rod guide. The container has a first end, a second end, and an inner volume that contains the medicament to be administered to a user. The nut has a first engagement region and a second engagement region. The trigger ring has a first engagement region that slidably engages the first engagement region of the nut and further has a second engagement region. The trigger ring also engages a portion of the shield such that it moves axially with the shield. The plunger rod guide has a first engaging region and an opening. The first engagement region of the plunger rod guide slidably engages the second engagement region of the trigger ring. The plunger rod guide is further operably coupled to a driving mechanism, which in some forms may be a power spring or a torque spring. Upon moving the shield, and thus the trigger ring, axially towards the distal end of the housing, the first engagement region of the trigger ring disengages from the first engagement region of the nut and/or the second engagement region of the trigger ring disengages from the first engagement region of the plunger rod guide, thereby causing the driving mechanism to urge the plunger towards the proximal end of the housing.

In some approaches, the trigger ring may be coupled to the nut such that relative rotation between the trigger ring and the nut is restricted while the first engagement region of the trigger ring engages the first engagement region of the nut. The trigger ring may also or separately be coupled to the plunger rod guide such that relative rotation between the trigger ring and the plunger rod guide is restricted while the second engagement region of the trigger ring engages the first engagement region of the plunger rod guide. In other examples, the trigger ring may slidably engage directly with the shell as opposed to the nut.

In examples, the peak resistance force is exerted within approximately a first 30% of the duration of an injection process that begins when the shield is initially moved axially and ends when the drive assembly completely administers the medicament. The shield may have a maximum axial travel towards the distal end of the housing of approximately 10 mm. In this example, the peak resistance force may occur within approximately the first 1 mm of travel of the shield. In other examples, the peak resistance force may occur at any point within the total range of motion leading up to activation of the device.

In some forms, the nut further includes at least one deflection finger that projects inwardly toward the longitudinal axis of the housing, and thus contacts an outer surface of the trigger ring. The at least one deflection finger can impart a force that is a combination of a frictional force and an axial reaction force on the nut that is sufficient to generate the peak resistance force prior to disengagement from the nut. In some examples, the peak resistance force may be generated by at least one of a frictional force exerted between the plunger rod guide and the trigger ring generated by the driving mechanism, a frictional force exerted between the trigger ring and the nut generated by the driving mechanism, an axial spring force exerted by a compression spring coupled to the shield, or a deflection force exerted by the nut. In still other forms, the drug delivery device may include a dose lockout mechanism that halts movement of the plunger rod upon moving the device in a direction towards the proximal end of the housing.

In accordance with a second aspect, a drive assembly for a drug delivery device includes a container having a first end and a second end, a nut positioned adjacent to the second end of the container, a trigger ring, a plunger rod guide, and a plunger rod. An inner volume of the container is adapted to contain a medicament to be administered to a user. The nut has a first engagement region and a second engagement region. The trigger ring has a first engagement region that slidably engages the first engagement region of the nut and further includes a second engagement region. The trigger ring is movable between a first position and a second position. The plunger rod guide has a first engaging region and an opening. The first engagement region of the plunger rod guide slidably engages the second engagement region of the trigger ring. The plunger rod guide is operably coupled to a driving mechanism. The plunger rod is at least partially disposed within the opening of the plunger rod guide. Upon moving the trigger ring in a first direction from the first position to the second position, at least one of the first engagement region of the trigger ring disengages from the first engagement region of the nut or the second engagement region of the trigger ring disengages from the first engagement region of the plunger rod guide. As a result the driving mechanism urges the plunger in a direction opposite from the first direction.

In accordance with a third aspect, a drug delivery device includes a housing defining a shell, an injection assembly (or pre-filled syringe) at least partially disposed in the housing, a shield, and a drive assembly at least partially disposed in the housing and coupled to the injection assembly and the shield. The injection assembly includes a needle or cannula. Upon moving the shield axially towards the distal end of the housing, a retraction profile commences where the drive assembly administers a medicament via the injection assembly. A peak resistance force is exerted prior to the needle or the cannula contacting a user's skin.

In accordance with a fourth aspect, a drug delivery device includes a housing, an injection assembly, a shield, and a drive assembly. The housing has a proximal end, a distal end, and a longitudinal axis extending between the proximal and distal ends. The Injection assembly is at least partially disposed within the housing at the proximal end thereof and includes a needle or a cannula having an endpoint. The shield assembly is coupled with the housing and has an extended position where at least a proximal end of the shield extends a distance beyond the proximal end of the housing. The drive assembly is also at least partially disposed within the housing and is operably coupled with the injection assembly and the shield. Upon moving the shield axially towards the distal end of the housing a predetermined distance, a retraction profile commences whereby the drive assembly administers a medicament via the injection assembly. A peak resistance force is exerted when an axial distance from the proximal end of the shield to the endpoint of the needle or the cannula, when measured in the distal direction, is less than or equal to approximately 12 mm.

BRIEF DESCRIPTION OF THE DRAWINGS

The above needs are at least partially met through provision of the activation and safety mechanism for a drug delivery device described in the following detailed description, particularly when studied in conjunction with the drawings, wherein.

Figure 8A:
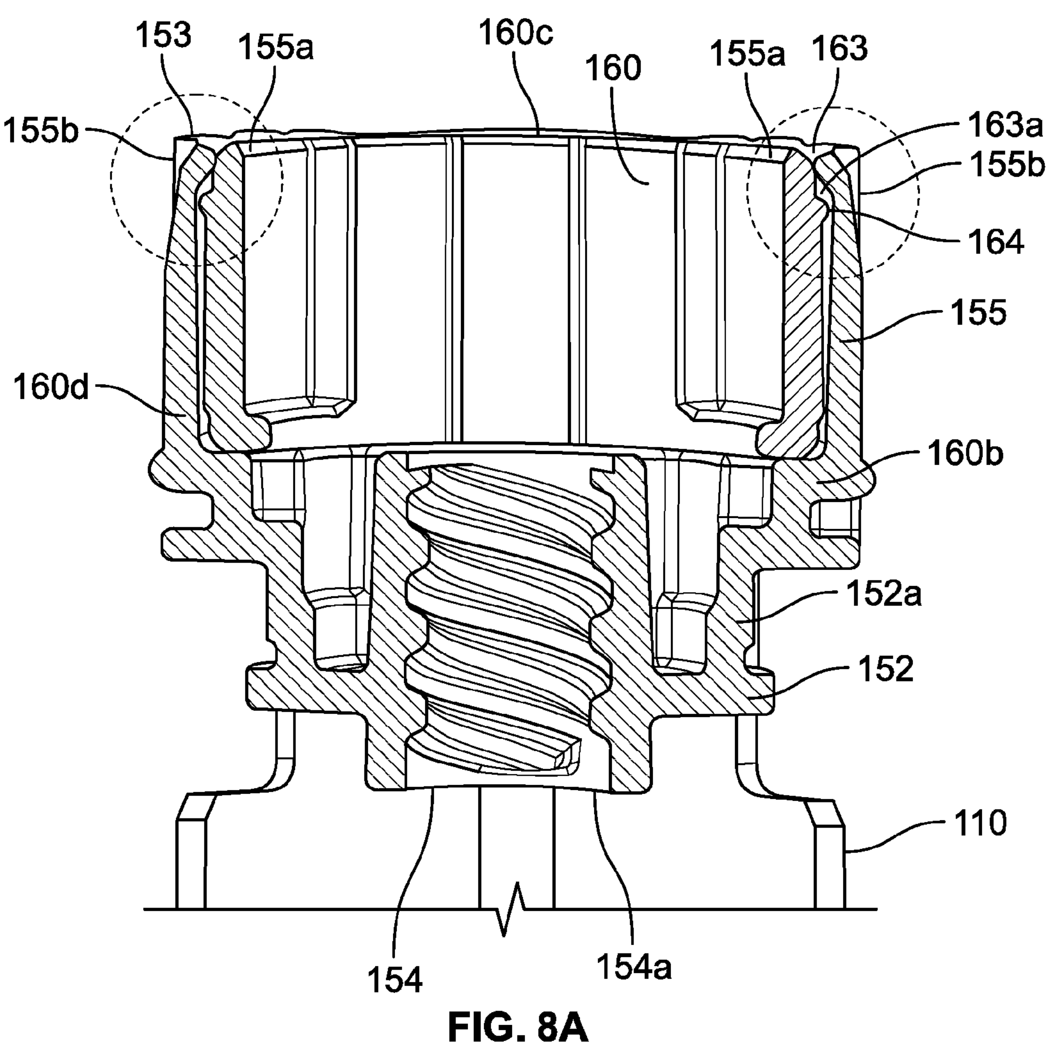
Figure 10:
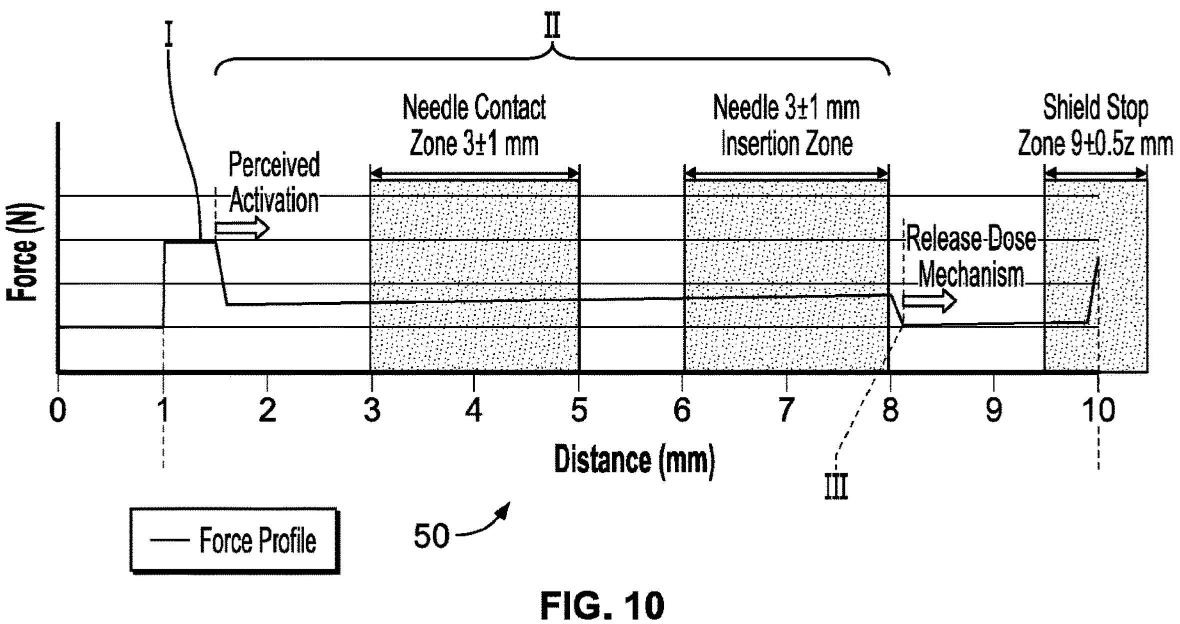
Figures 11, 12, 13A, 13B:
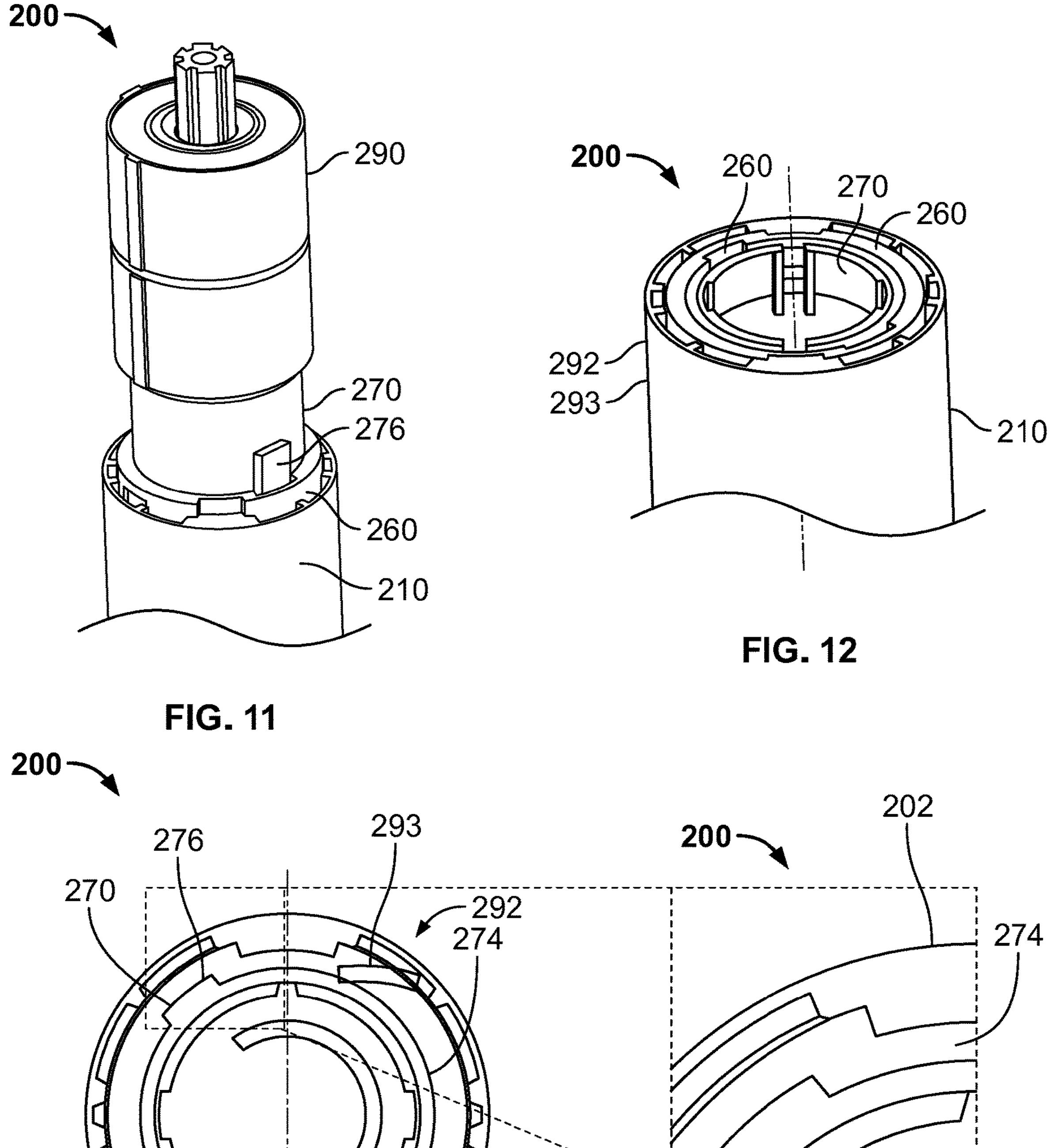

FIG. **8*a* is a front elevation cross sectional view of the drug delivery device of FIGS. 1-7** illustrating a portion of the drive assembly in accordance with various embodiments;

FIG. **8*b* is a front elevation view of the example drive assembly of FIG. 8*a*** in accordance with various embodiments;

FIGS. **9*a*-9*c* are perspective views of the drug delivery device of FIGS. 1-8*b*** illustrating activation of a drive mechanism in accordance with various embodiments;

FIG. 10 is an example force profile of the drug delivery device of FIGS. **1-9*c*** in accordance with various embodiments;

FIG. 11 is a perspective view of an example drug delivery device having an alternative drive assembly in accordance with various embodiments;

FIG. 12 is a perspective view of the example drive assembly of the drug delivery device of FIG. 11 in accordance with various embodiments;

FIG. 13*a* is a cross sectional view of the example drive assembly of the drug delivery device of FIGS. 11 and 12 in accordance with various embodiments; and FIG. 13*b* is a zoomed in view of the example drive assembly of FIG. 13*a* in accordance with various embodiments.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, an injector includes a housing, a container or syringe assembly containing a medicament to be injected into a user, and a rotatable drive or actuating assembly that uses a spring (e.g., a power spring or a torque spring) to cause the medicament to be injected into the user. The injector may be activated by axial movement (i.e., by pressing the injector against the injection site), and the injector provides sufficient feedback force against the injection site to allow a user to expect activation upon applying a sufficient force. The injector may only require a single step by the user for activation and requires a relatively low amount of force for both activating and holding the device during dosing, even when used in combination with high energy dosing mechanisms. Further, the activation elements are configured to reduce the likelihood of unintended injection due to inertial shocks such as when a device is dropped, which can be challenging to implement in a robust manner when using higher viscosity and higher energy systems.

As will be discussed in further detail, the described force profile also relies on a peak resistance force, or the maximum force opposing distal and/or axial movement of a shield during the retraction period, at the beginning of the retraction period, which serves a number of functions. First, requiring a peak resistance force at the onset of retraction works to improve the likelihood that the user will activate the device and insert the syringe fully once the user has overcome this peak resistance force due to the difference in force between the peak resistance force and the force required to retract the shield for the remaining travel distance. After the peak resistance force occurs, the force rapidly decreases so that the user is disinclined to remove the autoinjector 100. Put differently, the peak force occurs just prior to needle insertion, so the user has a limited timeframe to change their mind. Further, requiring a peak resistance force at the onset of retraction provides the user with a clear indication that the device has been activated.

Figure 1:
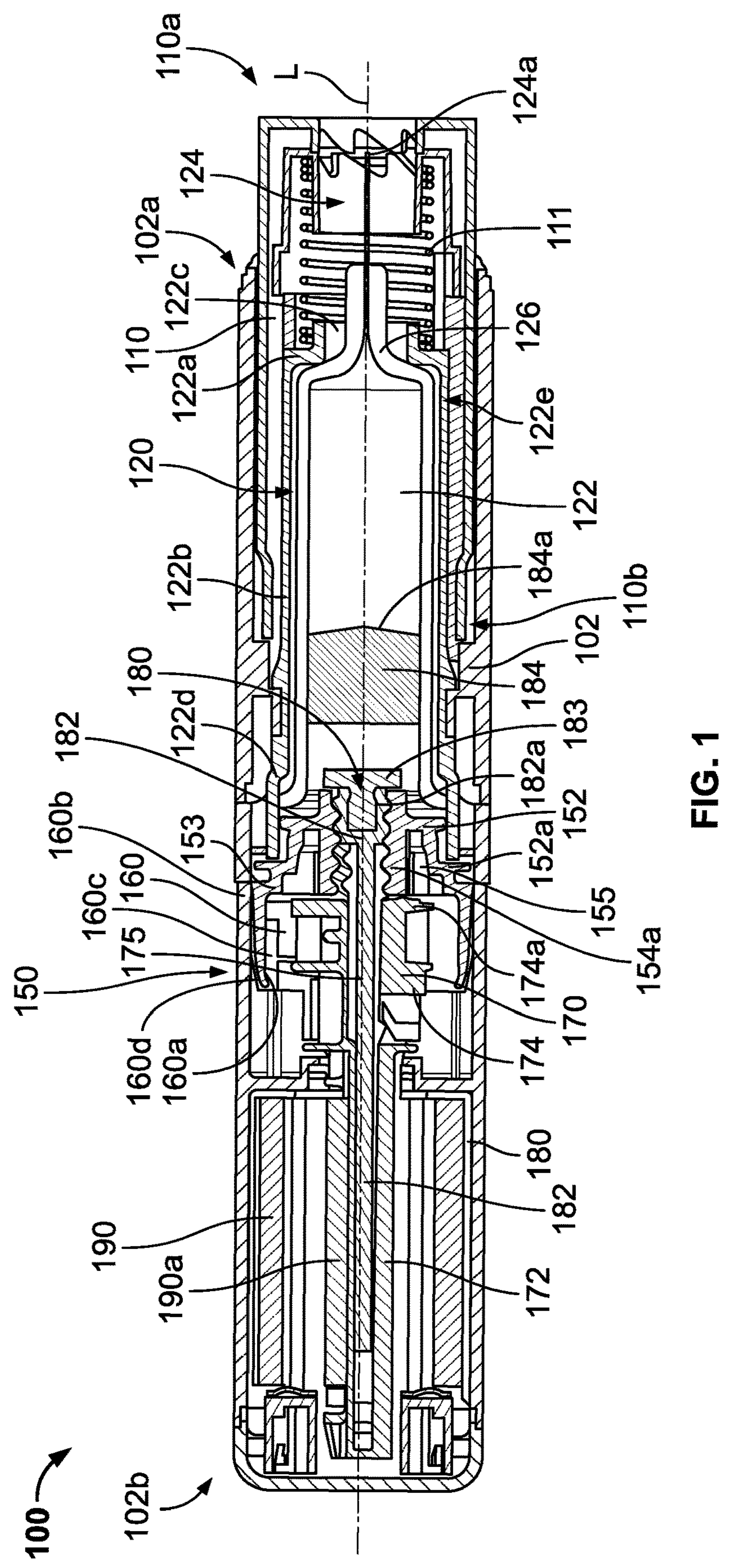
FIG. 1 illustrates a schematic representation of an example arrangement of a drug delivery device having an activation and safety mechanism in accordance with various embodiments.
Figure 2:
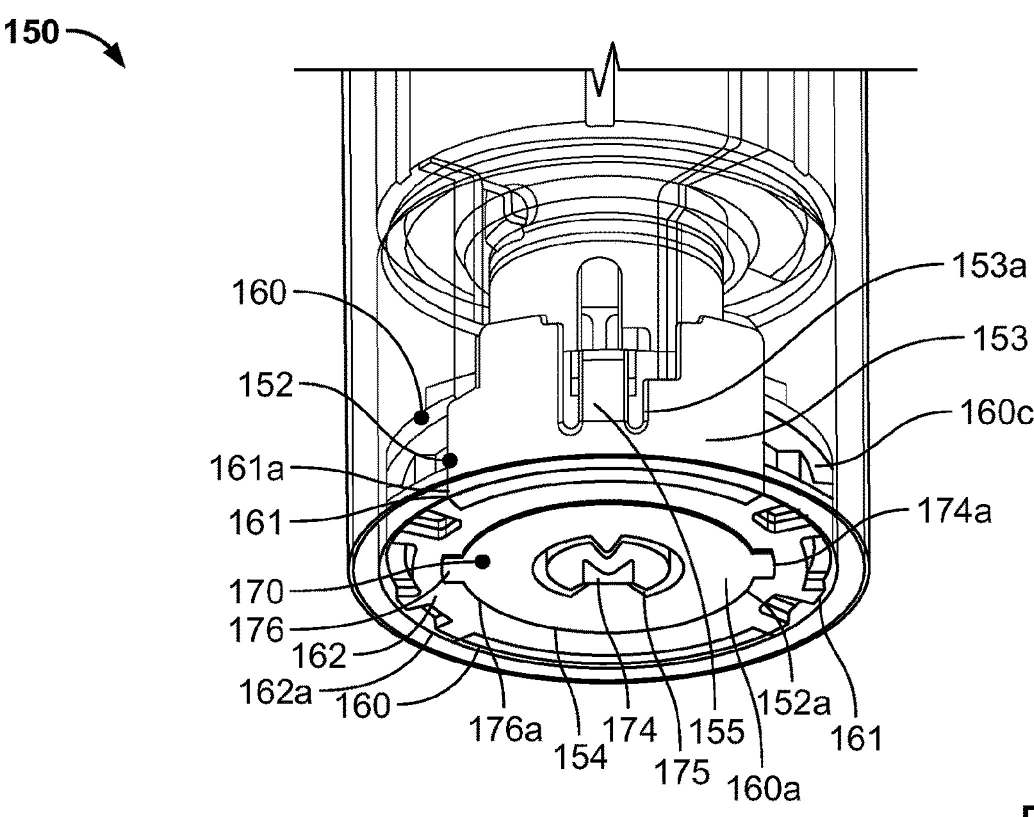
FIG. 2 is a perspective view of an example drive assembly of the drug delivery device of FIG. 1 in accordance with various embodiments.
Figure 2:
Figure 3:
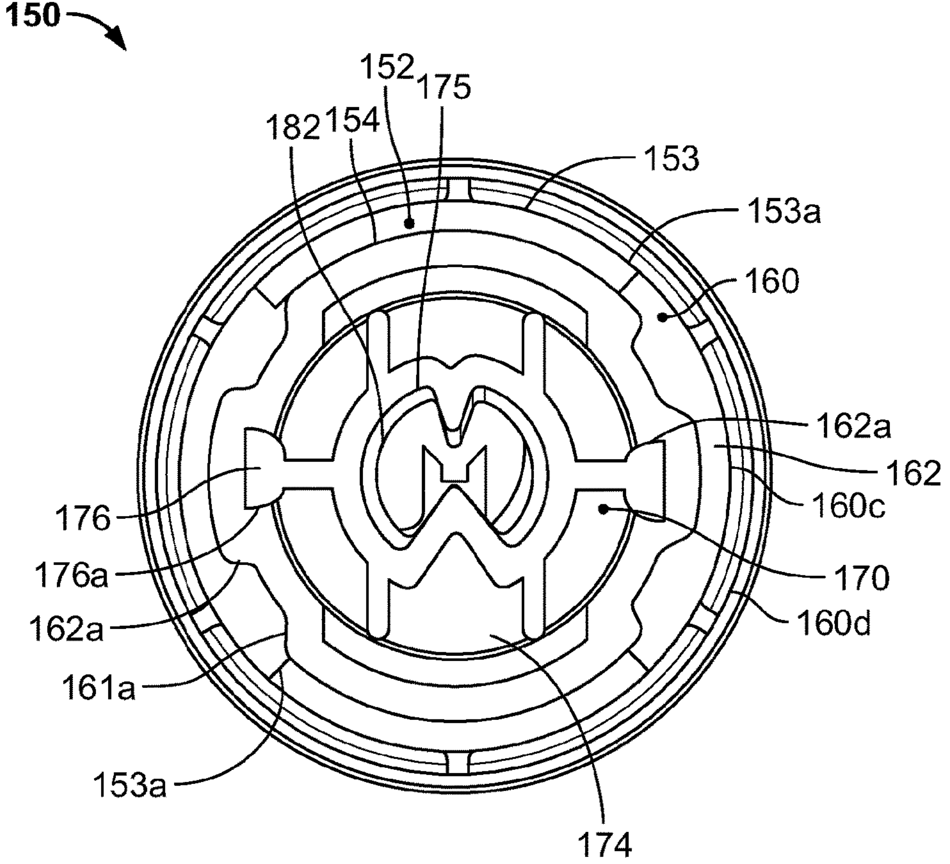
FIG. 3 is a cross-sectional view of the drive assembly of the drug delivery device of FIGS. 1 and 2 in accordance with various embodiments.

Referring to FIGS. 1-3, an example autoinjector 100 includes a housing 102 defining a shell, a shield 110, an injection assembly 120 (e.g., a pre-filled syringe), and a drive assembly or actuating mechanism 150. At least a portion of the shield 110, the injection assembly 120 and the drive assembly 150 are disposed within the housing 102. The housing 102 has a proximal end 102*a*, a distal end 102*b*, and a longitudinal axis "L" extending between the proximal and distal ends 102*a*, 102*b*. The shield 110 has a proximal end 110*a* and a distal end 110*b*. The injection assembly 120 includes a container or syringe barrel 122 and a needle or cannula 124 which has an endpoint 124*a*. In some examples, the injection assembly 120 may include a syringe barrel 122, a needle or a cannula 124, and a plunger 184. At least a portion of these components may be at least partially disposed in the housing 102. The drive assembly 150 is operably coupled to the shield 110 and the injection assembly 120. Any number of additional components (e.g., a shield spring 111, a syringe holder, a shield lock, filter members, etc.) may be used to assist in the operation of the autoinjector 100.

The syringe barrel 122 stores a medicament to be injected into a user. In the illustrated example, the syringe barrel 122 includes a base 122*a* and a sidewall 122*b* that define a cavity to store the medicament. Further, the syringe barrel 122 may include at least one opening 122*c* disposed through the base 122*a* to allow the medicament to pass into the needle or cannula 124. An end 122*d* of the syringe barrel 122 may be open to accommodate a plunger assembly 180, which will be described in further detail below. The syringe barrel 122 may be any desired shape and/or size to accommodate various quantities of medicament. In some examples, the syringe barrel 122 can be constructed from a cyclic-olefin polymer ("COP"). Other examples of materials are possible.

The needle or cannula 124 is coupled to a second end 122*e* of the syringe barrel 122 via any type of coupling mechanism and/or structure (e.g., a needle hub 126). The needle hub 126 defines a cavity that allows medicament to enter into the needle 124 via any number of openings. The needle hub 126 is positioned below the opening 122*c* formed in the base 122*a* of the syringe barrel 122. So configured, the needle hub 126 receives the medicament as it exits the syringe barrel 122, which then enters into the needle or cannula 124 to be administered to the user. It is understood that the injector 100 may include any number of additional components such as return springs, additional needle shields and/or guards, and the like to assist in administering the medicament to the user. For the sake of brevity, these additional components will not be discussed in substantial detail.

In some examples, the drive assembly 150 includes the container or syringe barrel 122, a nut 152 positioned adjacent to the end 122*d* of the syringe barrel 122, a trigger ring 160, a plunger rod guide 170, a plunger rod assembly 180, and a drive mechanism 190. The nut 152 may be fixedly coupled to the housing 102 via any number of approaches. In some arrangements, the nut 152 may be formed integrally with the housing 102. The nut 152 may have a base portion 152*a* and at least one tab 153 extending therefrom in a generally axial direction, an opening 154, and, as illustrated in FIGS. 2 and 8, may optionally include at least one flexible and/or resilient finger 155 that is inwardly biased towards the opening 154. The nut 152 may be constrained and/or secured within the device 100 via a frictional or other coupling to the housing 102. In some examples, the resilient finger 155 may be a part of the shell 102. In yet other examples, the trigger ring 160 may carry a deflection finger (not illustrated) that deflects outwardly towards the shell 102. Other examples are possible.

The at least one tab 153 defines a first engagement region 153*a*. More specifically, the first engagement region 153*a* is defined by an edge or side surface of the at least one tab 153. Further, the opening 154 may define a second threaded engagement region 154*a* (FIGS. 1 and 8), and the at least one finger 155 defines a third engagement region 155*a* at a distal end 155*b* thereof.

The trigger ring 160 is also disposed within the shell of the housing 102 and includes a top or first surface 160*a*, a bottom or second surface 160*b*, a body 160*c* extending therebetween that defines an inner surface 160*d* and an outer surface 160*e*. As seen in FIGS. 2 and 3, the body 160*c* of the trigger ring 160 is in the form of a generally cylindrical ring having a generally circular inner surface 160*d* and any number of ledges, protrusions, and grooves disposed around and/or inside the circumference of the ring. As an example, the trigger ring 160 may include a first ledge 161 disposed near the bottom 160*b* that defines a first engagement region 161*a*. The trigger ring 160 may further include any number of grooves 162 formed by the inner surface 160*d* that define a second engagement region 162*a* as well as any number of grooves 163 (FIGS. 5 & 8) formed by the outer surface 160*e* that define a third engagement region 163*a*. In the illustrated example of FIG. 8*a*, a stop 164 in the form of a circumferential bump or protrusion is positioned adjacent to the groove or grooves 163.

The trigger ring 160 may be coupled to the shield 110 via any number of techniques. For example, the bottom surface 160*b* of the trigger ring 160 may abut the distal end 110*b* of the shield 110. In other examples, the trigger ring 160 may include a securing component to secure the shield 110 thereto. Further, the first engagement region 161*a* of the trigger ring 160 slidably engages the first engagement region 153*a* of the nut 152.

The plunger rod guide 170 includes a rod portion 172 and a base portion 174 coupled thereto. The plunger rod guide 170 includes an opening 175 extending at least partially through the rod portion 172 and the base portion 174. The base portion 174 includes a lower surface 174*a* having any number of projections or tabs 176 (FIGS. 2 & 3) extending therefrom. The projection or projections 176 define a first engagement region 176*a* that slidably engages the second engagement region 162*a* of the trigger ring 160. For example, the projection or projections 176 of the base portion 174 may be disposed within the groove or grooves 162 of the trigger ring, which allow for relative axial movement while restricting relative rotational movement.

The plunger rod assembly 180 includes a plunger rod 182, a washer 183, and a plunger 184 that are moveable along the longitudinal axis L of the device 100. The plunger rod 182 has a threaded portion 182*a* which is threadably coupled to and is disposed within the opening 175 of the plunger rod guide 170 and the threaded opening 154 of the nut 152. The washer 183 minimizes frictional losses between rotation of the plunger rod 182 and the non-rotating plunger. In some approaches, the washer 183 may also be used to adjust the volume of medicament by making the washer 183 thicker or narrower. Accordingly, the washer 183 may be used to accommodate a range of fill volumes of medicament in the same device, thereby allowing for better control of the air gap between the bottom of the washer 183 and the top of the plunger 184. The rod portion 172 of the plunger rod guide 170 is coupled to the plunger assembly 180 via any number of approaches including, for example, via a splined connection or slotted arrangement that allows for the plunger assembly 180 to be axially displaced relative to the plunger rod guide 170. As such, the plunger rod guide 170 guides rotational movement of the plunger assembly 180. The threaded portion 182*a* of the plunger rod 182, and correspondingly, the threaded opening 154 of the nut 152 may have a thread pitch suitable for any desired drug delivery rate or force/torque combination when driven by the drive mechanism 190. Relative rotation between the plunger rod 182 and the nut 152 causes the plunger rod 182 to advance axially towards the proximal end 102*a* of the housing 102. The plunger 184 has a top face 184*a* that is disposed near the first end 122*d* of the syringe barrel 122.

In the illustrated example, the drive mechanism 190 is in the form of a power spring or a torque spring 190 having an inner portion 190*a* coupled to the rod portion 172 of the plunger rod guide 170 via any known approach to exert a torque on the plunger rod guide 170 to cause the plunger rod guide 170 to rotate about axis L. In some examples, the torque spring 190 may have a high number of turns to provide an appropriate rotational travel required to expel the medicament from the syringe barrel 122, however, additional parameters of the spring design may influence its torque output such as material properties and any applied heat treatments. The pre-shaping of the torque spring 190 may also impact its performance. As an example, in an autoinjector, a pre-stressed spring may be preferred, because the pre-stressing process generally increases torque output of the spring by initial coiling the spring in an opposite direction of the intended working condition, thereby causing permanent deformation in the steel band. This deformation maximizes the stresses in the material, thereby causing the torque to increase. Such an increase in torque is beneficial to minimize device size and weight.

In some examples, the torque spring 190 may have between approximately 1 and approximately 30 turns in the wound or loaded configuration, and preferably, approximately 12 turns. In some examples, the total spring turns may be higher due to a margin in both ends of the working range of approximately 20%, which may result in the range being between approximately 1*1.4=1.4 to 30*1.4=42. The dose mechanism turns are derived from the pitch and the required travel length. As previously stated, a smaller pitch is preferred due to requiring a low torque input and activation force. Accordingly, the activation force also will be lower. If a high axial force is not needed, the pitch can be raised and require fewer spring turns, thus allowing the device to be smaller. In some examples, the torque spring 190 may have a number of initial or preload turns to have a usable torque. After the preload turns, the torque spring 190 is further wound with working turns, or turns that are used in the device during injection. As a non-limiting example, the torque spring 190 may have approximately 2.5 preload turns and approximately 6 working turns. As such, the total number of turns during assembly is approximately 8.5. However, due to potentially large tolerances in the angular positioning of spring terminations, the torque spring 190 may have an initial play before reaching a solid state, and thus may have a total of approximately 10 turns. Devices having different drug volumes and viscosities may need a different average torque generated from the torque spring 190 if the same dosing is desired. The average torque output may be controlled by adjusting the width of the band used for the torque spring 190 (e.g., the axial length of the torque spring 190 when disposed in the device), and maintaining the same number of working turns. Doing so may allow different springs to be used with the same configuration as the device and have similar injection times while the volume and/or viscosity of the drug may be modified.

In some examples, the energy (EFLOW) required to expel the drug through a needle is determined by any combination of the drug volume, viscosity, needle flow path dimensions, and the targeted dosing time. The energy (ESPRING) that the torque spring 190 delivers may be determined by any combination of the number of working turns (N) and the average spring torque during the working turns (T). The energy delivered by the spring may be calculated using the following formula: ESPRING=2*Tr*N*T. If frictional losses are excluded in the system, the following relationship exists: EFLOW=ESPRING=2*π*N*T. Accordingly, the following relationship results: EFLOW/(2*π)=N*T. In other words, to have sufficient energy in the torque spring 190 to expel a given drug in a given volume through a given needle in a given time, the product (N*T) remains constant, and thus the higher torque may be converted to fewer working turns.

The threaded interface between the plunger rod 182 and the nut 152 provides a translation between the input torque of the torque spring 190 and the output axial force. By providing a torque spring 190 with a high turn count, it will have a lower overall torque as well as a smaller change in start and end torque as compared to a linear spring having comparable gearing specifications or other torsion springs with few turns and a lower pitch. Additionally, the threads of the plunger rod 182 and the nut 152 can have a lower pitch due to the increase in turn count, while still achieving the same linear motion of the plunger assembly 180. If the thread pitch is low, a smaller input torque is necessary to provide the same output force as a high pitch thread and high torque spring. Accordingly, the high turn count (e.g., between approximately 1 and approximately 30 turns), low torque system described herein allows for reduced activation forces, as the activation force is directly related to the input torque that must be used to drive the plunger assembly 180. Additionally, internal structural forces required to resist the torque from the torque spring 190 during storage (e.g., prior to use) is reduced, thus allowing for smaller injector designs to be used and for less expensive raw materials to be used. Additionally, the threaded interface between the plunger rod 182 and the nut 152 allows the threaded plunger rod 182 to be adjusted to accommodate for varying quantities of medicament stored in the syringe barrel 122. If necessary, the threaded plunger rod 182 may be initially installed at a lower position in injectors 100 having lesser drug product volumes disposed in the syringe barrel 122. Accordingly, the number of unique components is reduced, and variation management is simplified. The threaded plunger rod 182 may also be adjustably installed at various depths during the manufacturing and/or assembly process as needed.

As illustrated in FIGS. 1-5 and 8, when the device 100 is in a loaded configuration (that is, when the torque spring 190 is in a wound configuration), the torque spring 190 is restricted from rotating via its coupling to the rod portion 172 of the plunger rod guide 170. The plunger rod guide 170 is restricted from rotating due to the engagement between the projection or projections 176 (and thus the first engagement region 176*a*) of the base portion 174 of the plunger rod guide 170 and the groove or grooves 162 (and thus the second engagement region 162*a*) of the trigger ring 160. Further, the trigger ring 160 is rotationally restricted from movement due to the engagement between the ledge 161 (and thus the first engagement region 161*a*) of the trigger ring 160 and the at least one tab 153 (and thus the first engagement region 153*a*) of the nut 152, which is secured to the housing 102 in a non-rotatable manner. In addition, the at least one finger 155 of the nut 152 is at least partially retained within the at least one groove 163 on the outer surface 160*e* of the trigger ring 160 such that the third engagement region 155*a* of the nut 152 engages the third engagement region 163*a* of the trigger ring 160.

Figures 6, 7:
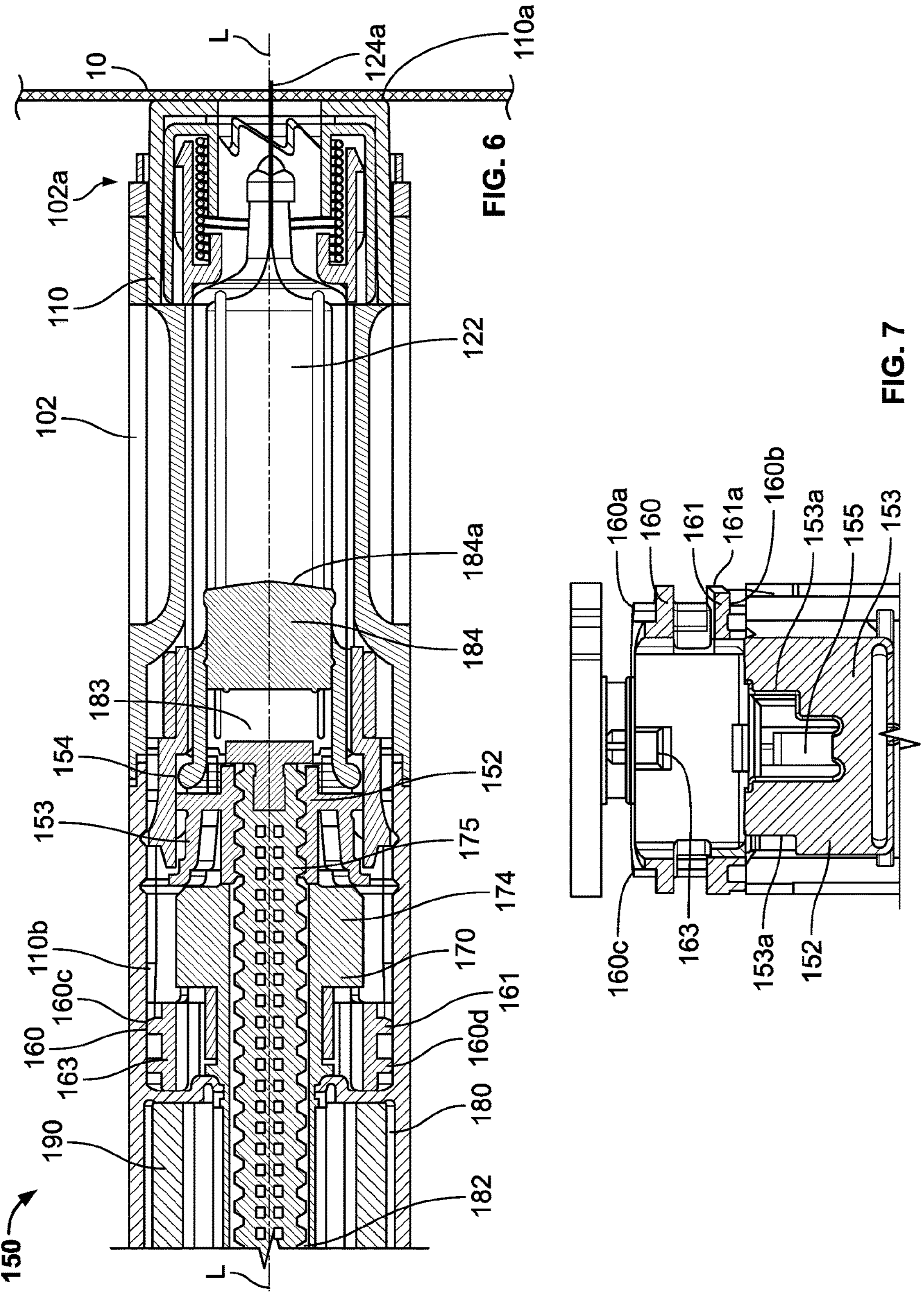
FIG. 6 is a cross-sectional view of the drug delivery device of FIGS. 1-5 in an activated configuration in accordance with various embodiments.
FIG. 7 is a front elevation view of the drug delivery device of FIGS. 1-6 in the activated configuration in accordance with various embodiments.

Turning to FIGS. 6 and 7, to administer the medicament, a user presses the device 100 against their skin (10 in FIG. 6), thereby urging the shield 110 towards the distal end 102*b* of the housing 102 and commencing a retraction profile. Continued urging of the shield 110 causes both the shield 110 and the trigger ring 160 to move towards the distal end 102*b* of the housing 102. In the extended configuration, at least the proximal end 110*a* of the shield 110 extends a distance beyond the proximal end 102*a* of the housing 102. Because the first engagement region 161*a* of the trigger ring 160 slidably engages the first engagement region 153*a* of the nut 152 and the second engagement region 162*a* of the trigger ring 160 slidably engages the first engagement region 176*a* of the plunger rod guide 170, the trigger ring 160 moves axially or slides relative to the nut 152 and the plunger rod guide 170. The trigger ring 160 must be moved axially to the point where it no longer rotationally constrains the nut 152 and/or the plunger rod guide 170. Continued axial movement causes the first engagement region 161*a* of the trigger ring 160 to disengage from the first engagement region 153*a* of the nut 152 and/or the second engagement region 162*a* of the trigger ring 160 to disengage from the first engagement region 176*a* of the plunger rod guide 170. As used herein, the term "retraction profile" is the point at which the device 100 is activated such that the injection process has begun and/or will proceed without further external input. For example, FIG. 6 shows the device 100 in its activated state such that the retraction profile has commenced. As a more specific example, in the above-described operation the retraction profile commenced when shield 110 axially moved to a point whereby the trigger ring 160 no longer rotationally constrains the nut 152 and/or the plunger rod guide 170. In other configurations or examples, the retraction profile may commence based on or due to different conditions.

In some examples, the trigger ring 160 may disengage from the plunger rod guide 170 at approximately the same time that it disengages from the nut 152. However, in other examples, the trigger ring 160 may disengage from the plunger rod guide 170 prior to the trigger ring 160 disengaging from the nut 152, and vice-versa. In some examples, the trigger ring 160 needn't disengage from the nut 152, and operation of the device 100 may continue as intended. In examples where the trigger ring 160 only disengages from the nut 152, the trigger ring 160 will rotate with the plunger rod guide 170. In examples where the trigger ring 160 only disengages from the plunger rod guide 170, the trigger ring 160 may continue to be rotationally locked to the nut 152.

Additionally, as the trigger ring 160 moves towards the distal end 102*b* of the housing 102, the at least one finger 155 begins to deflect outwardly and disengage from the at least one groove 163 of the trigger ring 160. The at least one finger 155 continues to deflect outwardly as it moves over the stop 164 disposed on the trigger ring 160.

Figures 9A, 9B, 9C:
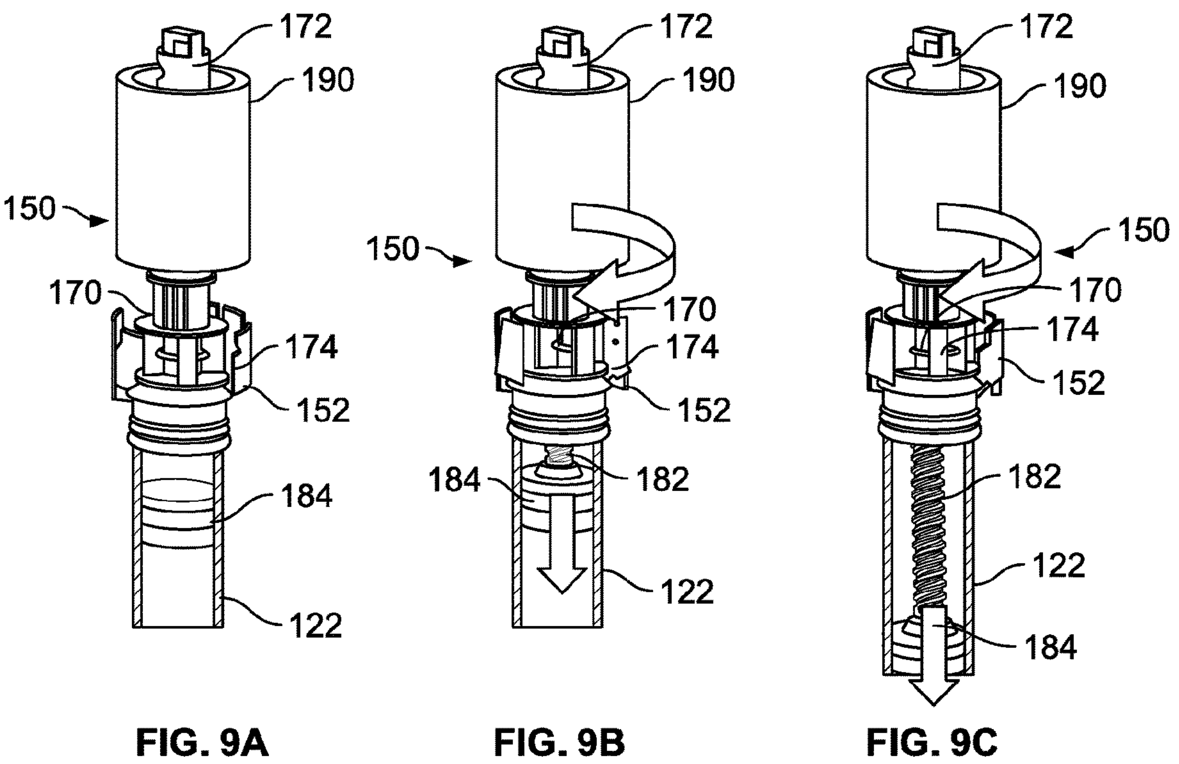

As illustrated in FIGS. 9*a*-9*c*, upon the trigger ring 160 disengaging from the nut 152 and the plunger rod guide 170, rotation of the watch spring 190 is permitted, which in turns causes the plunger rod guide 170 to rotate. This rotation in turn causes the plunger rod 182 to rotate, which, due to the threaded interface between the plunger rod 182 and the nut 152, causes the plunger rod 182 and the plunger 184 to advance from the first end 122*d* of the syringe barrel 122 to the second end 122*e* thereof, thereby inserting the needle or cannula 124 and administering the medicament.

During this activation process (i.e., commencement of the retraction profile), a user must overcome a number of forces that contribute to the resistance experienced when urging the shield 110 due to the mechanical interactions between components (i.e., resistance force). For example, key contributors to the total force required by the user at any point during the injection process include frictional forces between the trigger ring 160 and the plunger rod guide 170 resulting from the static load from the torque spring 190. This force may be approximately constant during retraction until the dosing mechanism is released, at which point the components disengage and the force drops to a much lower resistance force for the remainder of the injection process. Further, frictional forces between the trigger ring 160 and the nut 152 which result from the static load from the watch spring 190 also contribute to the total force required. This force is also constant during retraction until the dosing mechanism is released, at which point the parts disengage and the force drops to a much lower resistance force for the remainder of the injection process. The force required to compress the shield spring 111 also contributes to the total force required. This force gradually increases throughout the injection process as the spring continues to be compressed. Further still, the force required to deflect the resilient finger 155 as it disengages from the groove 163 and/or the stop 164 of the trigger ring 160 contribute to the total force required. This force may be in the form of a frictional force and/or an axial reaction force. In some examples, to provide for low variability on the experienced force, the reaction force may be used as the primary contributor to the force profile. In other words, low-friction materials may be used to reduce or minimize frictional forces. Other examples are possible. In examples where the deflection finger is a part of the trigger ring 160, the finger may induce an axial reaction and/or a frictional force against the nut 152 and/or the shell 102. Other approaches are possible.

Figure 4:
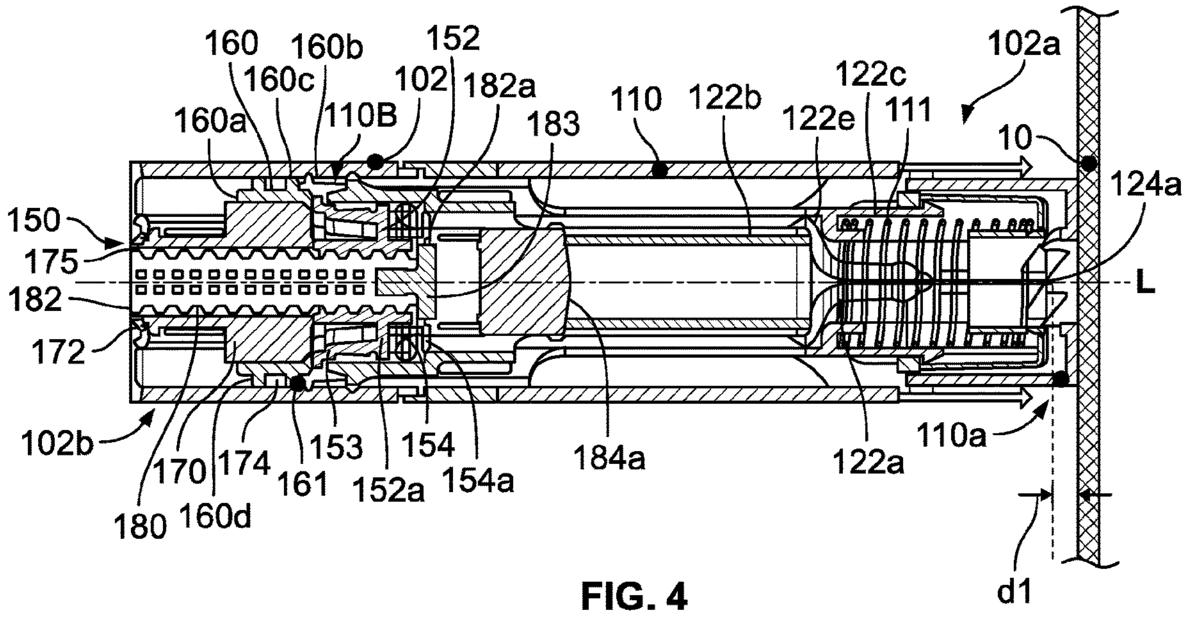
FIG. 4 is a cross-sectional view of the drug delivery device of FIGS. 1-3 in a loaded configuration in accordance with various embodiments.
Figure 5:
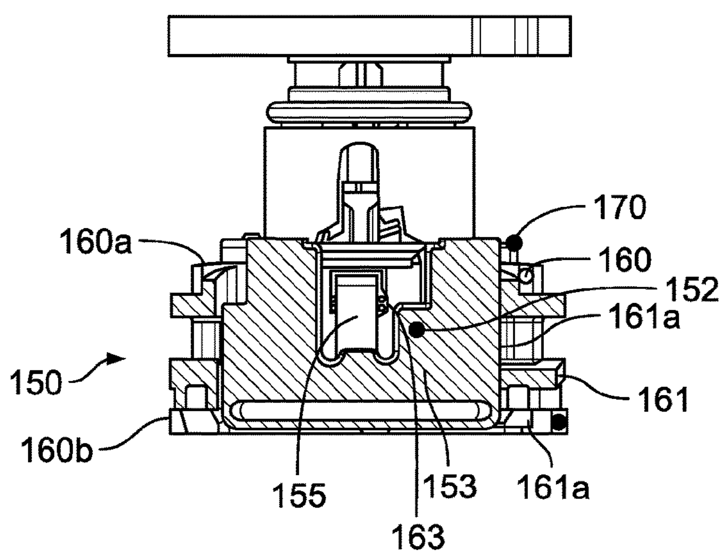
FIG. 5 is a front elevation view of the drug delivery device of FIGS. 1-4 in the loaded configuration in accordance with various embodiments.

As illustrated in FIG. 10, an example shield force profile 50 is provided that plots retraction displacement (mm) against force (N). The force profile 50 is but one example of desired force and displacement values, and thus it is understood that these values may vary depending on the design of the previously-noted interactions. Nonetheless, as shown in FIG. 10, the initial resistance force is relatively low for the first approximately 1 mm of travel by the shield 110, whereupon the resistance force quickly increases to a peak resistance force (denoted by "I" in FIG. 10) exhibited at the start or onset of the retraction period (e.g., within the first approximately 1-3 mm of shield 110 travel) that subsequently decreases within a short distance (e.g., within approximately an additional 1 mm-2 mm of shield 110 travel), thereby resembling a "quick trigger" effect. In some examples, the peak resistance force is exhibited within approximately the first 30% of shield 110 travel. In other examples, the peak resistance force is exhibited at any point within the full range of motion leading up to activation of the device 100. In yet other examples, the peak resistance force is exhibited at any point prior to the needle or cannula contacting a user's skin. In still other examples, and as illustrated in FIG. 4, an axial distance "di" is defined as a distance from the proximal end 110*a* of the shield 110 to the endpoint 124*a*. In these examples, the peak resistance force is exerted when the distance "di", when measured in the distal direction, is less than or equal to approximately 12 mm, and preferably, the peak resistance force is exerted within approximately the first 8 mm of axial movement of the shield, and more preferably, the peak resistance force is exerted within approximately the first 3 mm of axial movement of the shield. It is understood that in FIG. 4, the illustrated distance di is greater than approximately 3 mm. It is further understood that in other configurations such as, for example, the configuration in FIG. 6 where the end point 124*a* of the needle 124 is already past the needle shield 110, the distance di may be a negative number (and therefore less than 3 mm). After reaching the peak resistance force value, the force profile 50 continues with a period of gradually increasing forces (denoted by "II" in FIG. 10). At a point "μl", the force drops upon release of the dosing mechanism and is followed by a final lower force retraction period where the force gradually increases. At the end of the force profile 50, the force increases suddenly, as the shield 110 is restricted from further moving into the housing 102.

The example force profile 50 of FIG. 10 also illustrates how the use of the described drive assembly 150 allows for clearly defined shield displacement zones. In these zones, certain interactions occur which can be controlled through the specification of tolerances and proper dimensioning of parts. As an example, FIG. 10 shows that the point of dosing release is specified to occur after the minimum needle insertion zone, thus ensuring that the needle tip is inserted beyond the minimum depth before any medicament is expelled. In the illustrated example, a force both before and after the peak force are as low as possible to ensure users do not attempt to change their mind.

As previously noted, the peak resistance force value may be generated by the combination of any number of component interactions. Specifically, the principle of beam deflection, where the at least one finger 155 of the nut 152 are forced to outwardly deflect by the at least one groove 163 and/or the bump 164 of the trigger ring 160 as the trigger ring 160 is moved towards the distal end 102*b* of the housing 102, causes the force to increase to a peak level. Using the beam deflection principle for generating the peak resistance force allows for the expected peak resistance force to be calculated using a relatively simple calculation that depends on the surface friction of the two parts, the angle of the slope, and the amount of overlap between the two geometries that causes the beam deflection, the geometry and/or dimensions of the at least one finger 155 (e.g., a length, a width, etc.), and the material stiffness of the at least one finger 155.

Figure 8B:
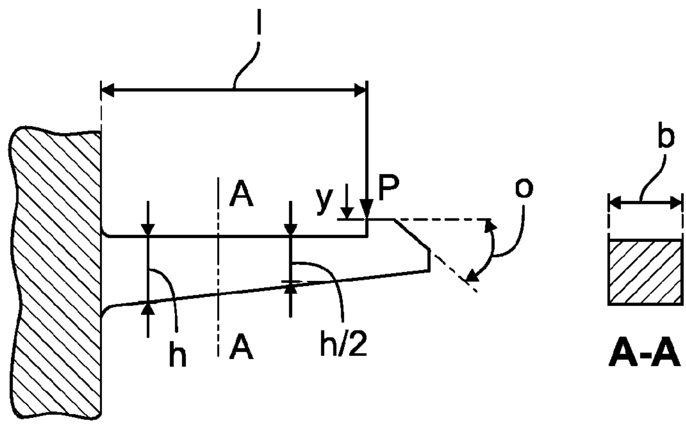

An example finger 155 is illustrated in FIG. 8*b* having a number of variables. In some examples, the peak resistance force may be calculated according to the following mathematical models:

Parameters for Deflecting Finger Contribution to Peak Resistance Force

| | |
|---|---|
| Distance from base to finger protrusion | $l := 5$ mm |
| Finger base thickness: | $h := 1.1$ mm |
| Displacement (peak) | $y_{peak} := 0.5$ mm |
| Protrusion angle | $a := 40$ deg |
| Finger width | $b := 1.5$mm |

-continued

| | |
|---|---|
| Young's Modulus | Es := 2500 MPa |
| Coefficient of friction | $\mu_{nut\ trig\ ring} = 0.1$ |
| Strain | $\epsilon := 1.5 \cdot \frac{y_{peak} \cdot h}{2l^2} = 0.017$ |
| Deflection force | $F_{deflection1} := 2 \cdot \frac{b \cdot h^2}{6} \cdot \frac{E_S \cdot \epsilon}{l} = 4.991N$ |
| Axial reaction force | $F_{friction} = F_{deflection} \cdot \tan\alpha = 4.19N$ |
| Friction force | $F_{friction} = F_{deflection} \cdot \frac{\mu_{nut\ trig\ ring} + (\mu_{nut\ trig\ ring} \cdot \tan^2(\alpha))}{1 - (\mu_{nut\ trig\ ring} \cdot \tan(\alpha))} = 0.93N$ |
| Separation force | $F_{separation} = F_{reaction} + F_{friction} = 5.12N$ |

Other examples of contributing factors to the absolute value of the peak resistance force include a shield spring force, a sliding force from the trigger ring against the plunger rod guide, a sliding force from the trigger ring against a frame component (e.g., the nut or the housing). Other examples are possible. Further, using this deflection arm principle to generate a peak resistance force is also beneficial during assembly and for increasing design robustness, as the at least one finger 155 assists in securing the trigger ring 160 and ensuring that it moves with the nut 152 during assembly as the nut 152 is pushed back and forwards during the winding and locking of the torque spring 190. The at least one finger 155 also ensures the device 100 cannot be accidentally activated if the device 100 is dropped or probed and/or inspected by the user. Further, the at least one finger 155 may be adjusted to modify the peak force as needed. For example, the size, thickness, stiffness, material used, or other parameters of the finger 155 may be adjusted to modify the peak force. Such adjustments may be easier to perform compared to traditional spring adjustments.

As illustrated in FIGS. 11-13*b*, an alternate drug delivery device 200 is provided. The drug delivery device 200 includes similar features and elements as the drug delivery device 100, and thus have reference numerals with identical two-digit suffixes as those in the drug delivery device 100 of FIGS. 1-10. As such, for the sake of brevity, similar components will not be described in detail. The drug delivery device 200 may include additional components not illustrated in the Figures, and any components present in the device 200 may be incorporated into the device 100. In some examples, if a user was to remove the device from the injection site prematurely (i.e., before all of the medicament has been delivered), a spray of medicament will be seen exiting the needle as the dose continues, even though the user is not receiving the benefit.

The device 200 may include a dose lockout mechanism 292 in the form of a spring loaded tab 293 recessed within the housing 202. The spring loaded tab 293 is aligned with the plunger rod guide 270, and more specifically, with at least one projection 276 of the base portion 274 of the plunger rod guide 270. The spring loaded tab 293 abuts against the trigger ring 260. The spring loaded tab 293 remains hidden within the housing 202 with minimal or no interference with other components other than a minimal friction exerted during the insertion phase as the trigger ring 260 moves past the spring loaded tab 293 to interact with the shield 210.

In these examples, once activated, the trigger ring 260 will not follow the shield 210, and thus, as the shield 210 moves towards the proximal end 202*a* of the housing 202 (e.g., during removal of the device 200 from the injection site), the distal end 210*b* of the shield 210 passes the spring loaded tab 293 and allows it to protrude into the path of the at least one projection 276 of the plunger rod guide 270 (which is rotating until delivery of the medicament is completed). Once the at least one projection 276 rotates into the path of the spring loaded tab 293, movement of the plunger rod guide 270 is stopped via the interfering geometry.

In some examples, multiple spring loaded tabs 293 may be used to reduce the total travel of the plunger rod guide 270 from removal of the device 200 to dose lockout. Other combinations of plunger rod thread pitches and/or ribs on the plunger rod guide 270 may be used to provide variations in the response time of the system. In some examples, alternative approaches to dose lockout mechanisms may include increasing the force of the shield spring (not illustrated) and/or combining the trigger ring 260 and the shield 210 so that removal from the user results in reengagement of the trigger ring 260.

In some instances, the dose lockout mechanism 292 may be beneficial to cease delivery simultaneously, or nearly coincident with removal from the site. Such a mechanism 292 may be beneficial where the treatment is acute with high risks associated with under-delivery. Such a mechanism 292 may additionally simplify the design of companion "smart" device elements such as the capture of how much dose was delivered to the patient by saving the data in the form of residual volume levels in the container. Without such a dose lockout mechanism 292, the information becomes very time dependent upon multiple sensors monitoring the depth of insertion and delivery status for example, resulting in a more complicated system with faster processing requirements. Static information such as volume remaining after injection (and the inverse information of dose delivered to patient) may be read by a reusable companion system such as a sharps container outfitted with imaging, mass balance, or other sensors designed for such a purpose. Alternatively, or additionally, a smartphone app for example could be used to collect an image post-injection and analyze it for completeness of dose received, which may not be possible if the autoinjector always ejects the total volume regardless of insertion status. In the event of an injection error where the patient mistakenly removes the device before the entire dose is complete, a prescribing health care professional might want to understand how much of the dose was missed before determining the next course of action. A dose lockout mechanism 292 might cease delivery at specific states such as "removal from subcutaneous depth" or "removal from patient," for example, aligning the relative mechanical engagement of such mechanism to the needle or some relative proxy for the needle depth. Then, if questioned by the healthcare professional, a patient might review the autoinjector (which is now locked out for needle safety purposes) and relay the amount of remaining volume to the HCP based on graduations, indicator marks, or similar features visible to the user.

Another potential benefit of the dose lockout mechanism 292 is the provision of a secondary load bearing surface once the activation has completed. While it is important for the plunger rod 282 to support the force transfer from the torque spring 290 during the injection, plastic components may be subject to creep when exposed to high forces over long periods of time. If an injector is not disposed of immediately and the plunger rod creeps due to residual loading of the spring, it may be apparent via the window and cause the user an impression of a poor quality product even though it performed as intended. By incorporating a dose lockout feature, the torque spring 290 will be limited in how much it can turn after removal from the injection site and thus has a redundant support available for the residual force, reducing the risk of post-injection failures.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β17 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Xolair® (omalizumab); ET1211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/lL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, or BPS 804 (Novartis) and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BiTE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed is:

1. A drug delivery device comprising: a housing having a proximal end and a distal end and a longitudinal axis extending between the proximal end and the distal end thereof; an injection assembly at least partially disposed within the housing at the proximal end thereof, the injection assembly including a needle or a cannula having an endpoint; a shield slidably coupled with the housing, the shield having an extended position wherein at least a proximal end of the shield extends a distance beyond the proximal end of the housing; and a drive assembly at least partially disposed within the housing and operably coupled with the injection assembly and the shield, the drive assembly comprising: a nut; a trigger ring; a plunger rod guide operably coupled to a driving mechanism comprising a torque spring; and a plunger rod at least partially disposed within an opening of the plunger rod guide, wherein upon moving the shield axially towards the distal end of the housing a predetermined distance, a retraction profile commences whereby the drive assembly administers a medicament via the injection assembly, wherein a peak resistance force is exerted prior to the needle or cannula contacting a user's skin, and wherein the peak resistance force is generated by at least one of: a frictional force exerted between the plunger rod guide and the trigger ring generated by the driving mechanism; a frictional force exerted between the trigger ring and the nut generated by the driving mechanism; or a force generated by the nut and exerted between the trigger ring and the nut.

2. The drug delivery device of claim 1, wherein the peak resistance force is exerted within approximately the first 8 mm of axial movement of the shield or the first 3 mm of axial movement of the shield.

3. The drug delivery device of claim 1, wherein the drive assembly further comprises: a container disposed within the housing, the container having a first end and a second end, an inner volume of the container being adapted to contain the medicament to be administered to a user; the nut disposed within the housing and positioned adjacent to the first end of the container, the nut having a first engagement region and a second engagement region; the trigger ring disposed within the housing, the trigger ring having a first engagement region that slidably engages the first engagement region of the nut and a second engagement region, the trigger ring engaging a portion of the shield such that the trigger ring moves axially with the shield; and the plunger rod guide disposed within the housing, the plunger rod guide having a first engaging region and an opening, the first engagement region of the plunger rod guide slidably engaging the second engagement region of the trigger ring, wherein upon moving the shield axially towards the distal end of the housing, at least one of the first engagement region of the trigger ring disengages from the first engagement region of the nut or the second engagement region of the trigger ring disengages from the first engagement region of the plunger rod guide, thereby causing the driving mechanism to urge the plunger rod towards the proximal end of the housing.

4. The drug delivery device of claim 3, wherein the trigger ring is coupled to at least one of (a) and (b):

(a) the nut such that relative rotation between the trigger ring and the nut is restricted while the first engagement region of the trigger ring engages the first engagement region of the nut, or (b) the plunger rod guide such that relative rotation between the trigger ring and the plunger rod guide is restricted while the second engagement region of the trigger ring engages the first engagement region of the plunger rod guide.

5. The drug delivery device of claim 3, wherein the nut further comprises at least one deflection finger that projects inwardly toward the longitudinal axis of the housing, thereby contacting an outer surface of the trigger ring, and wherein the at least one deflection finger imparts a frictional force on the nut that is sufficient to generate the peak resistance force prior to disengagement from the nut.

6. The drug delivery device of claim 1, wherein an injection process begins when the shield is initially moved axially and ends when the drive assembly completely administers the medicament, wherein the peak resistance force is exerted within approximately a first 15% of the duration of the injection process.

7. The drug delivery device of claim 1, wherein the shield has a maximum axial travel towards the distal end of the housing of approximately 10 mm, and wherein the peak resistance force occurs within approximately the first 8 mm of travel of the shield.

8. The drug delivery device of claim 1, wherein the peak resistance force is exerted when a distance between the endpoint of the needle or cannula and the proximal end of the shield is one of (a) less than or equal to approximately 12 mm, (b) less than approximately 12 mm and greater than approximately 3 mm, (c) less than or equal to approximately 3 mm, or (d) less than 0 mm.

9. The drug delivery device of claim 1, wherein the peak resistance force is a maximum force across the entire retraction profile.

10. The drug delivery device of claim 1, further comprising a dose lockout mechanism including a tab disposed within the housing, wherein the dose lockout mechanism halts movement of the plunger rod upon moving the shield towards the proximal end of the housing.

11. A drug delivery device comprising: a housing defining a shell having a proximal end and a distal end and a longitudinal axis extending between the proximal end and the distal end thereof; an injection assembly at least partially disposed within the housing at the proximal end thereof, the injection assembly comprising a needle or a cannula; a shield slidably coupled to the housing, the shield extending a distance beyond the proximal end of the housing; and a drive assembly at least partially disposed within the housing and operably coupled to the injection assembly and the shield, the drive assembly comprising: a nut; a trigger ring; and a plunger rod guide operably coupled to a driving mechanism comprising a torque spring, wherein upon moving the shield axially towards the distal end of the housing, a retraction profile commences where the drive assembly administers a medicament via the injection assembly, wherein a peak resistance force is exerted prior to the needle or cannula contacting a user's skin, and wherein the peak resistance force is generated by at least one of: a frictional force exerted between the plunger rod guide and the trigger ring generated by the driving mechanism; a frictional force exerted between the trigger ring and the nut generated by the driving mechanism; or a force generated by the nut and exerted between the trigger ring and the nut.

12. The drug delivery device of claim 11, wherein the drive assembly further comprises: a container disposed within the shell, the container having a first end and a second end, an inner volume of the container being adapted to contain the medicament to be administered to a user; the nut disposed within the shell and positioned adjacent to the first end of the container, the nut having a first engagement region and a second engagement region; the trigger ring disposed within the shell, the trigger ring having a first engagement region that slidably engages the first engagement region of the nut and a second engagement region, the trigger ring engaging a portion of the shield such that the trigger ring moves axially with the shield; the plunger rod guide disposed within the shell, the plunger rod guide having a first engaging region and an opening, the first engagement region of the plunger rod guide slidably engaging the second engagement region of the trigger ring; and a plunger rod at least partially disposed within the opening of the plunger rod guide; wherein upon moving the shield axially towards the distal end of the housing, at least one of the first engagement region of the trigger ring disengages from the first engagement region of the nut or the second engagement region of the trigger ring disengages from the first engagement region of the plunger rod guide, thereby causing the driving mechanism to urge the plunger rod towards the proximal end of the housing.

13. The drug delivery device of claim 12, wherein the trigger ring is coupled to at least one of (a) and (b):

(a) the nut such that relative rotation between the trigger ring and the nut is restricted while the first engagement region of the trigger ring engages the first engagement region of the nut, or (b) the plunger rod guide such that relative rotation between the trigger ring and the plunger rod guide is restricted while the second engagement region of the trigger ring engages the first engagement region of the plunger rod guide.

14. The drug delivery device of claim 12, wherein the nut further comprises at least one deflection finger that projects inwardly toward the longitudinal axis of the housing, thereby contacting an outer surface of the trigger ring, and wherein the at least one deflection finger imparts a frictional force on the nut that is sufficient to generate the peak resistance force prior to disengagement from the nut.

15. The drug delivery device of claim 11, wherein an injection process begins when the shield is initially moved axially and ends when the drive assembly completely administers the medicament, wherein the peak resistance force is exerted within approximately a first 15% of the duration of the injection process.

16. The drug delivery device of claim 11, wherein the shield has a maximum axial travel towards the distal end of the housing of approximately 10 mm, and wherein the peak resistance force occurs within approximately the first 8 mm of travel of the shield.

17. The drug delivery device of claim 11, wherein the peak resistance force is exerted when a distance between an endpoint of the needle or cannula and the proximal end of the shield is one of (a) less than or equal to approximately 12 mm, (b) less than approximately 12 mm and greater than approximately 3 mm, (c) less than or equal to approximately 3 mm, or (d) less than 0 mm.

18. The drug delivery device of claim 11, wherein the peak resistance force is a maximum force across the entire retraction profile.

19. A drug delivery device comprising: a housing having a proximal end, a distal end, and a longitudinal axis extending between the proximal end and the distal end thereof; an injection assembly at least partially disposed within the housing at the proximal end thereof, the injection assembly including a needle or a cannula having an endpoint; a shield slidably coupled with the housing, the shield having an extended position wherein at least a proximal end of the shield extends a distance beyond the proximal end of the housing; and a drive assembly at least partially disposed within the housing and operably coupled with the injection assembly and the shield, the drive assembly comprising: a nut; a trigger ring; a plunger rod guide operably coupled to a driving mechanism comprising a torque spring, wherein upon moving the shield axially towards the distal end of the housing a predetermined distance, a retraction profile commences whereby the drive assembly administers a medicament via the injection assembly, wherein a peak resistance force is exerted just prior to the needle or cannula contacting a user's skin, and wherein the peak resistance force is generated by at least one of: a frictional force exerted between the plunger rod guide and the trigger ring generated by the driving mechanism; or a frictional force exerted between the trigger ring and the nut generated by the driving mechanism.

20. The drug delivery device of claim 19, wherein the drive assembly further comprises: a container disposed within the housing, the container having a first end and a second end, an inner volume of the container being adapted to contain the medicament to be administered to a user; the nut disposed within the housing and positioned adjacent to the first end of the container, the nut having a first engagement region and a second engagement region; the trigger ring disposed within the housing, the trigger ring having a first engagement region that slidably engages the first engagement region of the nut and a second engagement region, the trigger ring engaging a portion of the shield such that the trigger ring moves axially with the shield; the plunger rod guide disposed within the housing, the plunger rod guide having a first engaging region and an opening, the first engagement region of the plunger rod guide slidably engaging the second engagement region of the trigger ring; and a plunger rod at least partially disposed within the opening of the plunger rod guide; wherein upon moving the shield axially towards the distal end of the housing, at least one of the first engagement region of the trigger ring disengages from the first engagement region of the nut or the second engagement region of the trigger ring disengages from the first engagement region of the plunger rod guide, thereby causing the driving mechanism to urge the plunger rod towards the proximal end of the housing.

21. The drug delivery device of claim 20, wherein the trigger ring is coupled to at least one of (a) and (b):

(a) the nut such that relative rotation between the trigger ring and the nut is restricted while the first engagement region of the trigger ring engages the first engagement region of the nut, and (b) the plunger rod guide such that relative rotation between the trigger ring and the plunger rod guide is restricted while the second engagement region of the trigger ring engages the first engagement region of the plunger rod guide.

22. The drug delivery device of claim 19, wherein an injection process begins when the shield is initially moved axially and ends when the drive assembly completely administers the medicament, wherein the peak resistance force is exerted within approximately a first 15% of the duration of the injection process.

23. The drug delivery device of claim 19, wherein the shield has a maximum axial travel towards the distal end of the housing of approximately 10 mm, and wherein the peak resistance force occurs within approximately the first 8 mm of travel of the shield.

24. The drug delivery device of claim 19, wherein the peak resistance force is exerted when a distance between the endpoint of the needle or cannula and the proximal end of the shield is one of (a) less than or equal to approximately 12 mm, (b) less than approximately 12 mm and greater than approximately 3 mm, (c) less than or equal to approximately 3 mm, or (d) less than 0 mm.

25. The drug delivery device of claim 19, wherein the peak resistance force is a maximum force across the entire retraction profile.

* * * * *